US00PP17800P2

(12) United States Plant Patent
Meiland

(10) Patent No.: US PP17,800 P2
(45) Date of Patent: Jun. 12, 2007

(54) ***ACONITUM* PLANT NAMED 'CLOUDY'**

(50) Latin Name: *Aconitum carmichaelii*
Varietal Denomination: Cloudy

(75) Inventor: Jacobus Hendrikus Meiland, Noordwijkerhout (NL)

(73) Assignee: Inspiration Plant C.V., Lisse (NL)

( * ) Notice: Subject to any disclaimer, the term of this patent is extended or adjusted under 35 U.S.C. 154(b) by 0 days.

(21) Appl. No.: 11/323,158

(22) Filed: Dec. 30, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Aconitum* plant named 'Cloudy', characterized by its upright plant habit; thick and strong flowering stems; freely flowering habit; and light blue and white bi-colored flowers.

2 Drawing Sheets

Botanical designation: *Aconitum carmichaelii.*
Cultivar denomination: 'Cloudy'.

BACKGROUND OF THE INVENTION

The present Invention relates to a new and distinct cultivar of *Aconitum* plant, botanically known as *Aconitum carmichaelii,* and hereinafter referred to by the cultivar name Cloudy.

The new *Aconitum* is a naturally-occurring whole plant mutation of the *Aconitum carmichaelii* cultivar Arendsii, not patented. The new *Aconitum* was discovered and selected by the Inventor during the summer of 1985 as a single flowering plant within a population of plants of the cultivar Arendsii in a controlled environment in De Zilk, The Netherlands.

Asexual reproduction of the new cultivar by divisions harvested in De Zilk, The Netherlands since the autumn of 1985, has shown that the unique features of this new *Aconitum* are stable and reproduced true to type in successive generations.

SUMMARY OF THE INVENTION

Plants of the cultivar Cloudy have not been observed under all possible environmental conditions. The phenotype may vary somewhat with variations in environment such as temperature and light intensity without, however, any variance in genotype.

The following traits have been repeatedly observed and are determined to be the unique characteristics of 'Cloudy'. These characteristics in combination distinguish 'Cloudy' as a new and distinct cultivar:

1. Upright plant habit.
2. Thick and strong flowering stems.
3. Freely flowering habit.
4. Light blue and white bi-colored flowers.

Plants of the new *Aconitum* differ from plants of the parent, the cultivar Arendsii, primarily in flower color as plants of the cultivar Arendsii have solid blue-colored flowers.

Plants of the new *Aconitum* can be compared to plants of the *Aconitum* cultivar Bicolor, not patented. In side-by-side comparisons conducted in De Zilk, The Netherlands, plants of the new *Aconitum* had stronger and thicker stems and were less susceptible to pathogens than plants of the cultivar Bicolor.

BRIEF DESCRIPTION OF THE PHOTOGRAPHS

The accompanying colored photographs illustrate the overall appearance of the new *Aconitum,* showing the colors as true as it is reasonably possible to obtain in colored reproductions of this type. Colors in the photographs may differ slightly from the color values cited in the detailed botanical description which accurately describe the actual colors of the new *Aconitum.*

The photograph at the top of the first sheet comprises a side perspective view of a typical flowering plant of 'Cloudy' grown in a container.

The photograph at the bottom of the first sheet is a close-up view of a typical flowering stem of 'Cloudy'.

The photograph at the top of the second sheet is a close-up view of a typical flower of 'Cloudy'.

The photograph at the bottom of the second sheet are close-up views of the upper (left) and lower (right) surfaces of typical plants of 'Cloudy'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and the following description were about two years-old and grown in an outdoor nursery in Noordwijkerhout, The Netherlands during the late summer and early fall. During the production of the plants, day temperatures ranged from 14° C. to 26° C. and night temperatures ranged from 4° C. to 14° C.

Botanical classification: *Aconitum carmichaelii* cultivar Cloudy.

Parentage: Naturally-occurring whole plant mutation of the *Aconitum carmichaelii* cultivar Arendsii, not patented.

Propagation:

*Type cutting.*—By divisions.

*Time to initiate roots, summer.*—About one week at 15° C. to 20° C.

*Time to initiate roots, winter.*—About one month at 9° C.

*Rooting time.*—From divisions, it takes about 300 days to produce a rooted young plant.

*Root description.*—Freely branching; light brown in color.

*Tubers.*—Length: About 9.8 cm. Diameter: About 4.1 cm. Texture: Slightly rough. Color: N199C.

Plant description:

*Form.*—Upright perennial flowering plant; columnar with deeply dissected leaves; light blue and white bi-colored galeate flowers arranged on erect racemes.

*Plant height.*—About 85 cm.

*Plant diameter.*—About 24.5 cm.

*Vigor.*—Moderately vigorous.

*Basal stem description.*—Quantity per plant: About three basal flowering stems develop per plant. Length (vegetative): About 65 cm. Diameter: About 6 mm. Internode length: About 3.7 cm. Shape: Rounded. Strength: Strong. Texture: Pubescent. Color: 144A tinted with 176B to 176C.

*Foliage description.*—Leaves alternate, simple, generally symmetrical and deeply dissected. Length: About 11.5 cm. Width: About 11.1 cm. Shape: Deeply dissected, pedately lobed. Apex: Acute. Base: Hastate. Margin: Serrate. Texture, upper surface: Sparsely pubescent. Texture, lower surface: Mostly glabrous; margins, sparsely pubescent. Venation: Palamate; lacinate. Petiole: Length: About 2.6 cm. Diameter: About 3 mm. Color, developing and fully developed, upper surface: 137A to 139A; venation, 144A. Color, developing and fully developed, lower surface: 146B; venation, 146C. Petiole color, upper and lower surfaces: 144A.

Flower description:

*Appearance.*—Numerous, single galeate, flowers arranged in terminal racemes; zygomorphic. Flowers not persistent. Flowers face outwardly.

*Quantity of flowers.*—Freely flowering, about 16 flowers per inflorescence.

*Natural flowering season.*—Summer to fall in the Netherlands; flowering continuous.

*Fragrance.*—Not fragrant.

*Flower longevity on the plant.*—About ten days.

*Inflorescence height.*—About 20 cm.

*Inflorescence diameter.*—About 8.3 cm.

*Flower size.*—Height: About 4.8 cm. Width: About 2.1 cm. Depth: About 2.4 cm.

*Flower buds.*—Length: About 1.8 cm. Diameter: About 1 cm. Shape: Ovate. Color: 145A to 145B.

*Sepals.*—Appearance/arrangement: Five per flower, petaloid; one upper sepal, two lateral sepals and two lower sepals. Length: Upper sepal: About 2.2 cm. Lateral and lower sepals: About 1.9 cm. Width: Upper sepal: About 1.4 cm. Lateral sepals: About 2.5 cm. Lower sepals: About 1.3 cm. Shape: Upper sepal: Galeate; apex, rounded. Lateral sepals: Orbicular; apex, rounded. Lower sepals: Elliptic to broadly elliptic; apex, rounded broadly acute. Margin, all sepals: Entire. Texture, upper surface: Sparsely pubescence. Texture, lower surface: Pubescent. Color, when opening, upper and lower surfaces: Upper sepal: N155A tinged with 91B to 91C; apical splotch, 90C to 90D. Lateral and lower sepals: 91D; apical splotch, 90C to 90D. Color, fully opened, upper and lower surfaces: Upper sepal: N155A tinged with 90B; apical splotch, 90A to 90B; at the apex, N88A. Lateral and lower sepals: 91D; apical splotch, 90A to 90B; at the apex, N88A.

*Petals.*—Quantity per inflorescence: About two. Length: About 2.1 cm. Width: About 5 mm. Shape: Narrowly flabellate to narrowly spatulate. Apex: Emarginate. Base: Cuneate. Margin: Entire. Texture, upper and lower surfaces: Smooth; margins sparsely pubescent. Color, upper and lower surfaces: N88A; towards the apex, N155A.

*Pedicel.*—Length: About 3.9 cm. Diameter: About 2 mm. Angle: About 30° from vertical. Strength: Strong. Color: 144B; upper surface lightly tinted with 176D.

*Peduncles.*—Length: About 16 cm. Diameter: About 3 mm. Aspect: Upright. Strength: Strong. Color: 144A to 144B tinted with 176C to 176D.

*Peduncle.*—Length: About 6 cm. Diameter: About 2 mm. Aspect: About 30° from vertical. Color, upper surface: 143A slightly tinted with N200A. Color, lower surface: 143A.

*Reproductive organs.*—Stamens: Quantity: About 60. Filament length: About 1 cm. Filament color: 157D. Anther shape: Broadly oblong to reniform; basifixed. Anther length: About 1.5 mm. Anther color: 147B to 145A to 145B. Pollen amount: Scarce. Pollen color: Close to 156D. Pistils: Quantity: About five. Pistil length: About 3 mm. Style length: About 2.5 mm. Style color: 144C. Stigma shape: Pointed. Stigma color: 144C. Ovary color: 144B to 144C.

*Seed/fruit description.*—Seed and fruit development has not been observed.

Disease & pest resistance: Plants of the new *Aconitum* have not been noted to be resistant to pathogens and pests common to *Aconitum.*

Temperature tolerance: Plants of the new *Aconitum* have been observed to tolerate high temperatures of 35° C. and to be hardy to USDA Zone 4.

It is claimed:

1. A new and distinct cultivar of *Aconitum* plant named 'Cloudy', as illustrated and described.

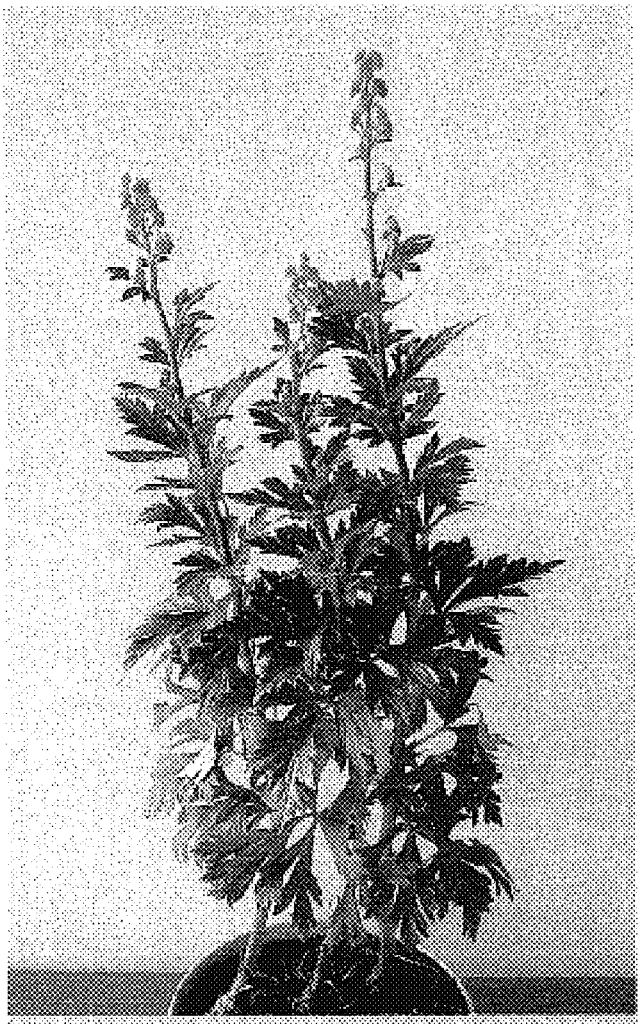
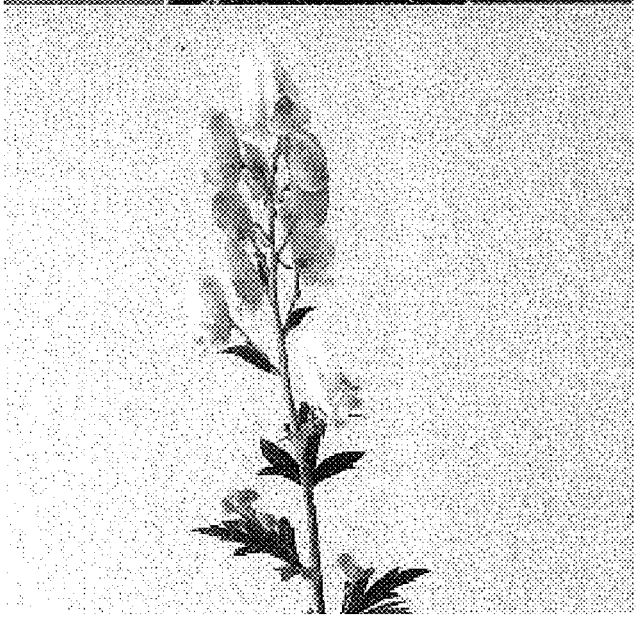

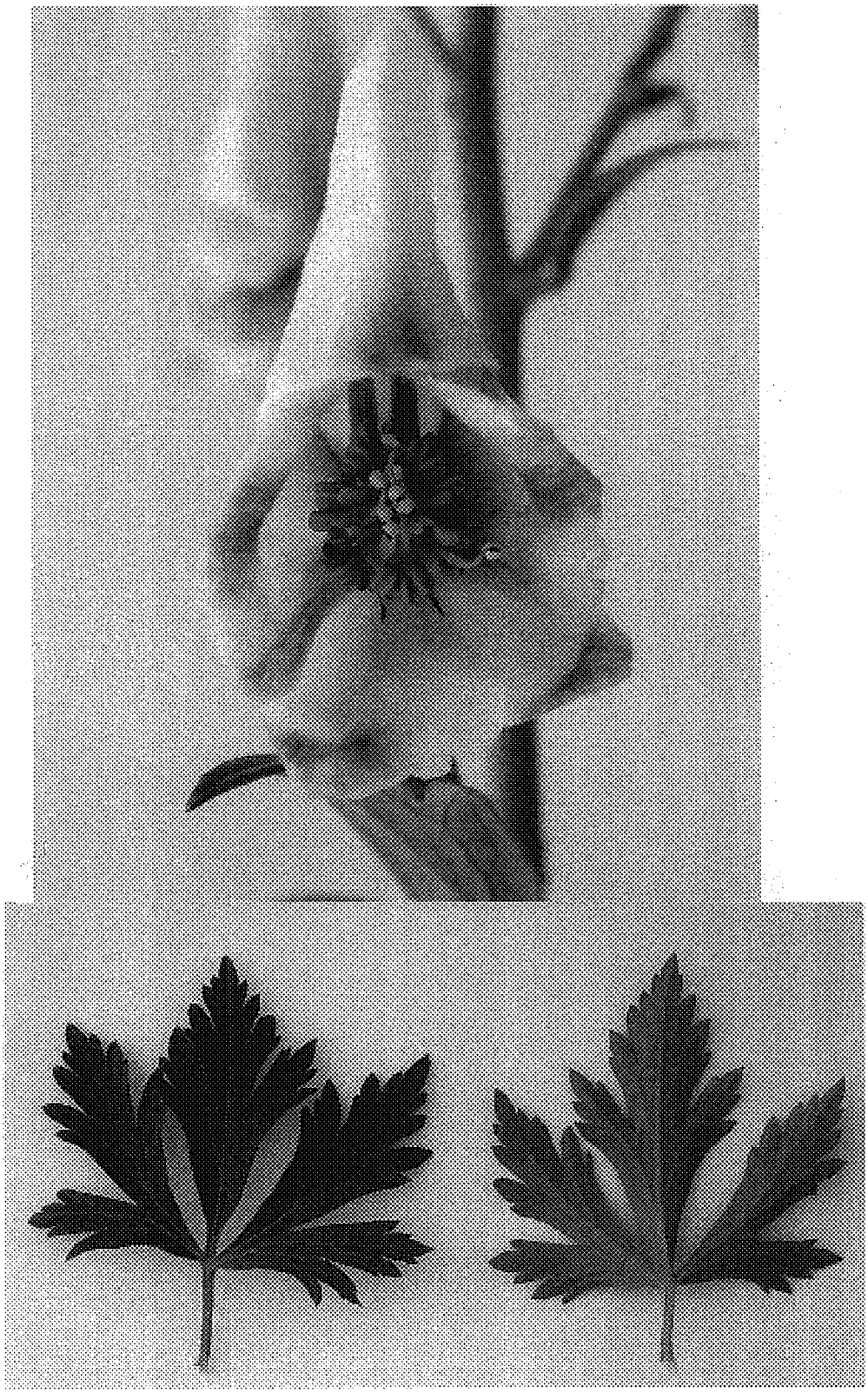

* * * * *